United States Patent [19]

Cavazza

[11] 4,330,557

[45] May 18, 1982

[54] ACYL-CARNITINE AND USE THEREOF IN PARENTERAL ADMINISTRATION OF TRIGLYCERIDES

[76] Inventor: Claudio Cavazza, 35, Via Marocco, 00144 Rome, Italy

[21] Appl. No.: 130,801

[22] Filed: Mar. 17, 1980

Related U.S. Application Data

[63] Continuation-in-part of Ser. No. 41,147, May 21, 1979, abandoned.

[51] Int. Cl.³ .......................................... A61K 31/205
[52] U.S. Cl. ..................................................... 424/316
[58] Field of Search ........................................ 424/316

[56] References Cited

U.S. PATENT DOCUMENTS

3,793,450  2/1974  Schnell ................................. 424/343
3,810,994  5/1974  Wiegand ............................... 424/316

*Primary Examiner*—Stanley J. Friedman
*Attorney, Agent, or Firm*—Ladas & Parry

[57] ABSTRACT

A composition for total or supplemental parenteral nutrition of patients in need thereof for the treatment of shock and trauma is disclosed. The composition comprises a therapeutically effective amount of triglycerides and an amount of an acyl-carnitine, typically acetyl-carnitine, or a pharmaceutically acceptable salt thereof sufficient to increase free fatty acid oxidation.

14 Claims, No Drawings

ACYL-CARNITINE AND USE THEREOF IN PARENTERAL ADMINISTRATION OF TRIGLYCERIDES

CROSS-REFERENCE

This is a continuation-in-part of Ser. No. 041,147 filed May 21, 1979, now abandoned.

BACKGROUND OF THE INVENTION

1. Field of the Invention

The present invention relates to a novel pharmaceutical composition for total or supplemental parenteral nutrition of patients in need thereof for treatment of shock and other trauma.

More particularly, the present invention relates to a novel composition for use in total or supplemental intravenous nutrition of patients in need thereof, such composition comprising a therapeutically effective amount of triglycerides. The present invention also relates to a therapeutical method of increasing the efficiency of triglyceride administration to patients in need thereof because of their condition of shock and trauma.

2. Description of the Prior Art

Up until recently, total parenteral nutrition was limited to the use of carbohydrates and protein hydrolysates, whereas intravenous administration of fats as caloric source was actually avoided in spite of its acknowledged utility based on the long-standing knowledge that several tissues, particularly the muscular tissue and the myocardium, utilize fatty acids as preferential energy substrate. Consequently, intravenous administration of exogenous fats would result in markedly beneficial effects in all those clinical situations wherein unbalanced conditions of some metabolic systems may occur.

One of these systems is for instance the adjustment system of the lipolysis whose role is that of furnishing suitable material to the tissues which utilize fatty acids and ketone bodies as energy source.

A second system, more closely related to the phenomena of the mitochondrial respiration, is the system wherein the carnitine-acetyl carnitine transferase complex plays an essential role. This complex is strictly related to the activity of ATP mitochondrial translocase and acts so as to allow the passage of the activated, long-chain free fatty acids through the mitochondrial membrane to take place and their attendant conveyance to the beta-oxidation sites.

The consequence brought about by the alterations of the abovementioned systems is the intracellular accumulation of long-chain fatty acids which, therefore, cannot be properly utilized. The muscular cells are thus deprived of an energy substrate of the utmost importance and muscular proteolysis is thereby enhanced with attendant loss of branched-chain aminoacids which are utilized by the muscular tissues for energy purposes. This impaired free fatty acid utilization causes the blockage of several enzyme systems of the mitochondrial walls and the onset of cardiac rhythm disturbances.

More recently, administration of triglycerides to patients affected by conditions of shock and trauma has become a problem of major concern and after extensive experimentation and researches lipid packs in the form of an intravenous emulsion of fats and oils have been developed and become commercially available. As an instance of useful lipid pack, Intralipid (marketed by Cutter Laboratoires, Berkeley, Calif.) can be cited. Intralipid is made up of 10% soybean oil (a mixture of the glycerides of oleic, linolic, palmitic, stearic and linolenic acids), 1.2 egg yolk phospholipids, 2.25% glycerin, the balance being water for injection, sufficient sodium hydroxide being added to adjust the pH to 5.5–9.0.

Other compositions of lipid packs at present available on the market are disclosed in "Total parenteral nutrition" by Parshotam L. Madan, Devendra K. Madan and Joseph F. Palumbo, Drug Intelligence and Clinical Pharmacy, Vol 10, Dec. 76, pages 684–696, and in "L'alimentation parenterale par émulsions lipidiques" by G. Duchesne, La Revue du Praticien (1974), 24, 5, pages 377–384. The disclosures of these articles are incorporated by reference in this specification.

Exogenous triglycerides of the intravenous fat emulsion are intended to be hydrolyzed in the body by lipase with attendant formation of glycerol and fatty acids. These latter should in turn undergo progressive oxidation.

SUMMARY OF THE INVENTION

It has been found however that the administration of lipid packs to patients in need of exogenous triglycerides frequently does not lead to therapeutically satisfactory results because of the sharply reduced clearance of triglycerides and free fatty acids by patients in shock and trauma, particularly by intensively catabolic patients (such as, e.g. those who have undergone extensive burns, fractures or major surgical operations). Reduced clearance of triglycerides and free fatty acid has been recently shown to occur also in premature and small for gestational age babies.

It is, therefore, one object of the present invention to provide a pharmaceutical, triglyceride-comprising composition which allows the efficiency of exogenous triglycerides administered to patients for treatment of shock and trauma to be increased.

It is a further object of the present invention to provide a triglyceride-comprising composition suitable to minimize or prevent adverse metabolic reactions to exogenous triglycerides, such as the depletion of endogenous carnitine in the heart and other muscular tissues that can take place as a consequence of lipid pack administration.

In accordance with the present invention, there has now been discovered a parenterally administrable pharmaceutical composition useful for providing nutrition to humans comprising an amount of physiologically acceptable triglycerides therapeutically effective for nourishing said humans, an amount of an acyl carnitine of the general formula

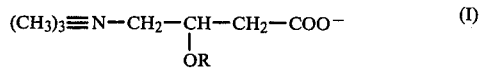

(I)

wherein R represents acetyl, propionyl, butyryl, hydroxybutyryl, hexanoyl, octanoyl, decanoyl, palmitoyl, stearoyl, acetoacetyl, succinyl, isovaleryl and crotonyl or a pharmaceutically acceptable salt thereof, sufficient to enhance free fatty acid oxidation, and a pharmaceutically acceptable carrier therefor.

The amount of the acyl-carnitine of formula (I) or the pharmaceutically acceptable salt thereof is from about 2 to about 30 g/l of parenterally administrable composition.

It has been found that exogenous acyl-carnitine of formula (I) enhances the efficiency of triglyceride administration, because acylcarnitine of formula (I) increases the oxidation rate of free fatty acids derived from exogenous triglycerides parenterally administered to patients for treatment of shock and trauma.

It has in fact been found that exogenous acyl-carnitine of formula (I) is suitable for re-activating the mitochondrial respiration processes because it supplies energy-releasing material (i.e. the acyl groups) which has direct access to the krebs cycle, and allows the passage of the long chain fatty acids through the mitochondrial membrane to be resumed, thus making possible the beta-oxidation processes to get started again.

It has furthermore been found that co-administration of exogenous acyl-carnitine of formula (I) and exogenous triglycerides is suitable to counterbalance or prevent the carnitine depletion in the muscular tissues, particularly in the myocardium, which can be brought about by the administration of lipid packs to patients in need thereof for the treatment of shock and trauma.

It should be understood that, within the scope of this invention, by the term "triglycerides" those glycerides are meant which are pharmacologically acceptable to a human and, furthermore, are of significance as far as the lipid requirements in the human diet are concerned.

The present invention also provides a method of treating patients in need of total parenteral nutrition, which comprises parenterally administering to a patient in need thereof an amount of physiologically acceptable triglycerides therapeutically effective for nourishing said patient and in combination therewith an amount of acyl-carnitine of the general formula

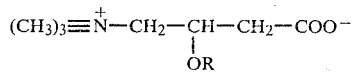

OR wherein R represents acetyl, propionyl, butyryl, hydroxy butyryl, hexanoyl, octanoyl, decanoyl, palmitoyl, stearoyl, acetoacetyl, succinyl, isovaleryl and crotonyl or a pharmaceutically acceptable salt thereof sufficient to enhance free fatty acid oxidation.

DESCRIPTION OF THE PREFERRED EMBODIMENTS

It has been found that lipid components particularly suitable for use in combination with the acyl-carnitines of formula (I) or a pharmaceutically acceptable salt thereof in the parenterally administrable compositions of this invention are soybean oil, cottonseed oil, sesame oil and safflower oil.

As known, these oils contain the glycerides of linoleic, oleic, linolenic and palmitic acids, the relative amounts of the various glycerides varying with the specific oil considered.

It is apparent that other pharmacologically acceptable, edible oils which comprise the foregoing glycerides may be used in the compositions of the present invention.

It has been also found that particularly suitable compositions for the total parenteral mutrition in accordance with the present invention are as follows:

| Composition 1 | |
|---|---|
| soybean oil | 50–200 g/l |
| glycerine | 22–26 g/l |
| egg yolk phospholipids (ovolecithin) | 10.5–12.5 g/l |
| acetyl-carnitine or pharmaceutically acceptable salt thereof | 5–25 g/l |
| sodium hydroxide | sufficient to adjust the pH of the composition to 5.5–9.0 |
| distilled water | balance to 1 liter. |

The composition thus obtained is an isotonic intravenous emulsion having an osmolarity of from about 250 to 330 milliosmoles/kg of distilled water.

| Composition 2 | |
|---|---|
| cottonseed oil | 100–200 g/l |
| soybean lecithin | 10–30 g/l |
| sorbitol | 40–60 g/l |
| D,L-α-Tocopherol | 0.5–1 g/l |
| acetyl-carnitine or pharmaceutically acceptable salt thereof | 5–25 g/l |
| Distilled water | Balance to 1 liter |

| Composition 3 | |
|---|---|
| Sesame oil | 100–200 g/l |
| Glycerine | 20–30 g/l |
| Cetylstearylsulfonic acid | 1–1.5 g/l |
| Propionyl-carnitine or pharmaceutically acceptable salt thereof | 3–20 g/l |
| Distilled water | Balance to 1 liter |

| Composition 4 | |
|---|---|
| Safflower oil | 100–200 g/l |
| Sorbitol | 50–70 g/l |
| Polysorbate | 8–12 g/l |
| D,L-α-Tocopherol | 0.5–1 g/l |
| Acetoacetyl-carnitine or pharmaceutically acceptable salt thereof | 2–20 g/l |
| Distilled water | Balance to 1 liter |

The desired daily dosage of the composition will be determined in accordance with standard usage, a daily dosage of 500 ml being generally sufficient.

According to a preferred embodiment, the method of treating patients in need of total parenteral nutrition comprises administering first the above specified emulsions and continuing carnitine administration for a total of 12 to 24 hours, after discontinuation of said triglyceride administration.

This will insure that sufficient carnitine is present to maintain high serum levels to increase triglyceride utilization and counterbalance any adverse metabolic effects of the triglycerides. Carnitine administration may be, therefore, started by intravenous perfusion and then continued by the oral or parenteral route.

As known, carnitine contains an asymmetric carbon atom and consequently exists in two stereoisomers. Either the racemate or the isolated isomers can be conveniently used in the method of the present invention, although it appears that the L-isomer is more active, while the D-isomer is slightly more toxic. Thus, the $LD_{50}$ in rats and mice assessed for various routes of administration according to the Litchfield and Wilcoxon method is as shown in the following Table A. (Litchfield, J. T., and Wilcoxon, F., J. Pharm. Exptl. Therap. 96, 99. 1949).

TABLE A

| product | animal | route | LD$_{50}$ (mg/kg) |
| --- | --- | --- | --- |
| D,L-carnitine | rat | i.v. | 995 |
| D-carnitine | " | sc | 10,000 |
| D,L-carnitine | mouse | i.v. | 610 |
| D,L-carnitine | " | sc | 6,000 |
| D-carnitine | " | sc | 5,400 |
| L-carnitine | " | sc | 7,000 |

The dose of acyl-carnitine which is administered will be determined by the attending physician having regard to the age, weight and condition of the patient, using sound professional judgement. Although effective utilization of exogenous glycerides can be noticed at doses as low as from 30 to 50 mg/kg of body weight daily, a dose of from about 150 to about 200 mg/kg of body weight daily is preferred. Should it be deemed necessary, larger doses can be safely administered, because of the extremely low toxicity of acyl-carnitine.

Some clinical studies are briefly summarized hereinbelow.

CASE 1

A 56 year old female patient was operated for removal of suppurated echinococcal cyst of the right lobe of the liver; after ten days of total parenteral nutrition initiated due to the severe sepsis exhibited by the patient: infusion was given via the central venous route of hypertonic glucose solution and a solution of amino acids and electrolytes for a total of 4000 ml daily with a 1:120 daily ratio of nitrogen: calories; via the peripheral route 500 ml of lipid emulsion (10%) containing acetyl carnitine 1.4% were infused every other day. Therapy was continued up to the 15th day after surgery and 4 days before the end normal cutaneous temperature was present and the patient had already begun to receive food through the mouth.

The following blood-composition parameters were checked on alternate days: glucose, BUN, Na+, K+, Ca+, protides, albumin, transaminase, alkaline phosphatase, total bilirubin, total lipids, total and esterified cholesterol, triglycerides, haemochromocytometric test. With the exception of glycaemia, maintaining values between 120 and 200 mg%ml, bilirubin between 2 and 4 mg%ml with 1.2 mg%ml on the 15th day and alkaline phosphatase constantly showing values around 150 U/ml also upon discharge (normal up to 80 U/ml), the other parameters exhibited values within the normal range. The following were determined 8 times on different during parenteral nutrition: cardiac output using the Fick method, total peripheral resistances, artherovenous O$_2$ difference, O$_2$ consumption.

These assessments showed constant presence of cardiovascular hyperdynamism (cardiac output constantly between 3.1 and 4.8 l/min/mg with O$_2$ consumption between 140 and 230 ml/min/mg) demonstrating the effectiveness and good tolerance of the hypercaloric nutritional therapy.

CASE 2

A 50 year old male patient was hospitalized with cancer of cardia in malnutritional conditions; for approximately 4 months he had been complaining of worsening dysphagia for solids and liquids with an almost total impossibility to feed himself during the last 20 days. The patient, weighing 50 kg upon admittance, was given total parenteral nutrition by means of central venous catheter positioned for sub-clavian artery puncture. Daily administration: 1000 ml of glucose solution 40%, 1000 ml of an amino-acid solution 8.5%, 500 ml of lipid emulsion 5% containing acetyl carnitine 0.7%, vitamins and electrolytes. The parenteral nutrition was clinically well tolerated without giving rise to abnormal blood values. The blood parameters were checked every other day. In particular nitrogen and creatinine, total lipid, triglyceride and carnitine blood values remained within normal values. Now and then the ketone body urine value was positive using the ketostix test carried out every 12 hours.

After 15 days of nutrition the patient was in good conditions for surgery and his body weight had increased by 8 kg.

CASE 3

A 40-year old male patient was hospitalized because of a severe starvation caused by "short bowel syndrome"; seven months earlier, he underwent a large resection of the small bowel after mesenteric vein occlusion of unknown origin. Since then, he kept on feeding by mouth, sometimes trying hypercaloric diets enriched with median-chain-triglycerides or desultory cycles of hypocaloric parenteral nutrition; he seemed not to benefit by this treatment and he went on losing weight.

By the time he came under our observation, he weighed 44 kg and he had 4–5 bowel movements each day, so that total daily volume of stools was approximately 5 liters.

Total serum albumin was very low (2.2 g%ml); serum potassium was low (2.7 mEq/l); alkaline phosphatases and serum transaminases were slightly increased; anaemia was not severe (Hb 10 g%ml), but serum iron levels were quite low. He soon began total parenteral nutrition through central venous catheter and he was put on n.p.o.

Over a period of 4–5 days daily administration gradually reached 600 to 700 g of glucose, 100 g of amino acids, 500 ml of 5% lipid solution containing 0.7% acetyl-carnitine (peripheral route), vitamins, minerals and electrolytes; the daily amount of water given through the various routes was somewhere between 3000 to 4000 ml.

Serum potassium levels returned to normal only after 30 days of administering 200 mEq of potassium per day. Diarrhoea receded after 12 days of this treatment and only little amounts of mucus were passed with the stools. After 25 days of treatment the central venous catheter was removed because of systemic sepsis, and lipids and amino acids were administered for five days via the peripheral route, while glucose was interrupted.

During this period, no particular alterations of serum values were observed: total lipids, serum triglycerides, total cholesterol and esters were always within the normal range. Parenteral nutrition by central venous catheter was begun again, though lipid 5% administration was changed to 500 ml of a 20% lipid solution with 2.1% acetyl-carnitine, twice weekly. For a further two months, parenteral nutrition was continued according to this schedule: minor changes involved electrolytes, glucose, and addition of insulin or albumin; the antral vanous catheter was replaced twice.

After three months of total parenteral nutrition, our patient weighed 54 kg; parenteral nutrition was interruptedn and he was fed on elementary diet. Though he continued to receive lipid administration for an additional week by the central venous route. One month after the beginning of this treatment, our patient had 2-3 bowel movements each day (nearly 1.5 liters on the whole) and body weight remained unchanged. He was discharged from hospital while on oral feeding (varied diet including few solid foods and precooked meat).

What is claimed is:

1. In the method of increasing in a human the level of fatty acids selected from the group consisting of oleic acid, linoleic acid, palmitic acid, stearic acid and linolenic acid by parenteral intravenous administration of one or more triglycerides of said fatty acid to a human, the improvement which comprises sumultaneously administering a quantity of an acyl-carnitine sufficient to enhance the oxidation of said fatty acids in the body of said human, said acyl-carnitine having the general formula

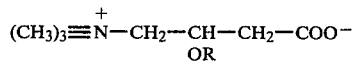

wherein R represents acetyl, propionyl, butyryl, hydroxy butyryl, hexanoyl, octanoyl, decanoyl, palmitoyl, stearoyl, acetoacetyl, succinyl, isovaleryl and crotonyl.

2. A method of treating patients in need of total parenteral nutrition, which comprises parenterally administering to a patient in need thereof an amount of physiologically acceptable triglycerides therapeutically effective for nourishing said patient and in combination therewith an amount of an acyl-carnitine of the general formula:

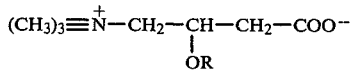

wherein R represents acetyl, propionyl, butyryl, hydroxy butyryl, hexanoyl, octanoyl, decanoyl, palmitoyl, stearoyl, acetoacetyl, succinyl, isovaleryl and crotonyl or a pharmaceutically acceptable salt thereof sufficient to increase free fatty acid oxidation.

3. The method according to claim 1, wherein said acyl-carnitine is an L-acyl-carnitine.

4. The method according to claim 1, which further comprises orally or parenterally administering daily for 12 to 24 hours after discontinuation of said triglyceride administration, from about 30 mg to about 200 mg of said acyl-carnitine per kg of body weight.

5. A parenterally administerable aqueous intravenous pharmaceutical composition for increasing in the body of a human recipient thereof the level of fatty acids selected from the group consisting of oleic acid, linoleic acid, palmitic acid, stearic acid and linolenic acid, said composition comprising a quantity of one or more triglycerides of said fatty acids sufficient upon hydrolysis in the body to afford a nutritionally effective amount of said fatty acid, and an amount of an acyl-carnitine or a pharmaceutically acceptable salt thereof sufficient to enhance the oxidation of said fatty acids in the body, said acyl-carnitine having the general formula

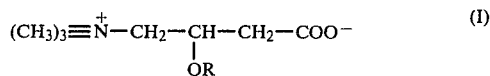

wherein R represents acetyl, propionyl, butyryl, hydroxy butyryl, hexanoyl, octanoyl, decanoyl, palmitoyl, stearoyl, acetoacetyl, succinyl, isovaleryl and crotony.

6. The composition according to claim 5, wherein said amount of acyl-carnitine or pharmaceutically acceptable salt thereof is from about 2 to about 30 g/l.

7. The composition according to claim 5 comprising:

| | |
|---|---|
| soybean oil | 50-200 g/l |
| glycerine | 22-26 g/l |
| egg yolk phospolipids (ovolecithin) | 10.5-12.5 g/l |
| acetyl-carnitine or a pharmaceutically acceptable salt thereof | 5-25 g/l |
| sodium hydroxide | sufficient to adjust pH of composition to 5.5-9.0 |
| distilled water | balance to 1 liter. |

8. The composition according to claim 5, comprising:

| | |
|---|---|
| cottonseed oil | 100-200 g/l |
| soybean lecithin | 10-30 g/l |
| sorbitol | 40-60 g/l |
| D,L-α-tocopherol | 0.5-1 g/l |
| acetyl-carnitine or pharmaceutically acceptable salt thereof | 5-25 g/l |
| distilled water | balance to 1 liter. |

9. The composition according to claim 5, comprising

| | |
|---|---|
| sesame oil | 100-200 g/l |
| glycerine | 20-30 g/l |
| cetylstearylsulfonic acid | 1-1.5 g/l |
| propionyl-carnitine or pharmaceutically acceptable salt thereof | 3-20 g/l |
| distilled water | balance to 1 liter |

10. The composition according to claim 5, comprising:

| | |
|---|---|
| safflower oil | 100-200 g/l |
| sorbitol | 50-70 g/l |
| polysorbate | 8-12 g/l |
| D,L-α-tocopherol | 0.5-1 g/l |
| acetoacetyl-carnitine or pharmaceutically acceptable salt thereof | 2-20 g/l |
| distilled water | balance to 1 liter |

11. The composition according to claim 5, wherein said acyl-carnitine is L-acyl-carnitine.

12. The composition according to claim 7, wherein said acetyl-carnitine is L-acetyl-carnitine.

13. The composition according to claim 8, wherein said acetyl-carnitine is L-acetyl-carnitine.

14. The composition according to claim 2, wherein said propionyl-carnitine is L-propionyl-carnitine.

* * * * *